US006225099B1

(12) United States Patent
Hummel et al.

(10) Patent No.: US 6,225,099 B1
(45) Date of Patent: May 1, 2001

(54) ALCOHOL DEHYDROGENASE AND ITS USE FOR THE ENZYMATIC PRODUCTION OF CHIRAL HYDROXY COMPOUNDS

(75) Inventors: Werner Hummel, Titz; Bettina Riebel, Cologne, both of (DE)

(73) Assignee: Forschungszentrum Jülich GmbH, Jülich (DE)

( * ) Notice: Subject to any disclaimer, the term of this patent is extended or adjusted under 35 U.S.C. 154(b) by 0 days.

(21) Appl. No.: 09/466,109

(22) Filed: Dec. 17, 1999

Related U.S. Application Data

(62) Division of application No. 08/822,322, filed on Mar. 21, 1997, now Pat. No. 6,037,158.

(30) Foreign Application Priority Data

Mar. 21, 1996 (DE) .............................................. 196 10 984

(51) Int. Cl.⁷ ....................................................... C12N 9/02

(52) U.S. Cl. .......................... 435/189; 435/190; 536/23.2; 536/23.7

(58) Field of Search .................................. 536/23.2, 23.7; 435/189, 190

(56) References Cited

U.S. PATENT DOCUMENTS 5,763,236 * 6/1998 Kojima et al. ....................... 435/148

* cited by examiner

Primary Examiner—Nashaat T. Nashed
Assistant Examiner—Christian L. Fronda
(74) Attorney, Agent, or Firm—Fulbright & Jaworski, LLP (57) ABSTRACT

Stable microbial enzyme with alcohol dehydrogenase activity having an activity maximum at ca. 50° C., process for its isolation and its use for the enantioselective reduction/oxidation of organic keto compounds/hydroxy compounds wherein, depending on the type of the starting compounds R- or S-hydroxy compounds are obtained. In particular an alcohol dehydrogenase obtainable from *Lactobacillus brevis* has proven to be suitable.

5 Claims, 2 Drawing Sheets

FIG. 1

```
ATG TCT AAC CGT TTG GAT GGT AAG GTA GCA ATC ATT ACA GGT GGT ACG
 M   S   N   R   L   D   G   K   V   A   I   I   T   G   G   T
TTG GGT ATC GGT TTA GCT ATC GCC ACG AAG TTC GTT GAA GAA GGG
 L   G   I   G   L   A   I   A   T   K   F   V   E   E   G
GCT AAG GTC ATG ATT ACC GGC CGG CAC AGC GAT GTT GGT GAA AAA
 A   K   V   M   I   T   G   R   H   S   D   V   G   E   K
GCA GCT AAG AGT GTC GGC ACT CCT GAT CAG ATT CAA TTT TTC CAA CAT
 A   A   K   S   V   G   T   P   D   Q   I   Q   F   F   Q   H
GAT TCT TCC GAT GAA GAC GGC TGG ACG AAA TTA TTC GAT GCA ACG GAA
 D   S   S   D   E   D   G   W   T   K   L   F   D   A   T   E
AAA GCC TTT GGC CCA GTT TCT ACA TTA GTT AAT AAC GCT GGG ATC
 K   A   F   G   P   V   S   T   L   V   N   N   A   G   I
GCG GTT AAC AAG AGT GTC GAA GAA ACC ACG ACT GCT GAA TGG CGT
 A   V   N   K   S   V   E   E   T   T   T   A   E   W   R
AAA TTA TTA GCC GTC AAC CTT GAT GGT GTC TTC TTC GGT ACC CGA TTA
 K   L   L   A   V   N   L   D   G   V   F   F   G   T   R   L
GGG ATT CAA CGG ATG AAG AAC AAA GGC TTA GGG GCT TCC ATC ATC
 G   I   Q   R   M   K   N   K   G   L   G   A   S   I   I
AAC ATG TCT TCG ATC GAA GGC TTT GTG GGT GAT CCT AGC TTA GGG GCT
 N   M   S   S   I   E   G   F   V   G   D   P   S   L   G   A
TAC AAC GCA TCT AAA GGG GCC GTA CGG ATT ATG TCC AAG TCA GCT
 Y   N   A   S   K   G   A   V   R   I   M   S   K   S   A
GCC TTA GAT TGT GCC CTA AAG GAC TAC GAT GTT CGG GTA AAC ACT GTT
 A   L   D   C   A   L   K   D   Y   D   V   R   V   N   T   V
CAC CCT GGC TAC ATC AAG ACA CCA TTG GTT GAT GAC CTA CCA GGG
 H   P   G   Y   I   K   T   P   L   V   D   D   L   P   G
GCC GAA GAA GCG ATG TCA CAA CGG ACC AAG ACG CCA ATG GGC CAT
 A   E   E   A   M   S   Q   R   T   K   T   P   M   G   H
ATC GCT GAA CCT AAC GAT ATT GCC TAC ATC TGT GTT TAC TTG GCT TCT
 I   A   E   P   N   D   I   A   Y   I   C   V   Y   L   A   S
AAC GAA TCT AAA TTT GCA ACG GGT TCT GAA TTC GTA GTT GAC GGT GGC
 N   E   S   K   F   A   T   G   S   E   F   V   V   D   G   G
TAC ACT GCT CAA
 Y   T   A   Q
```

FIG. 2

```
TDRLKGKVAIVTGGTLGIGLAIADKFVEEGAKVVITGRHA
DVGEK-X26-LFDATEEAFGPVTTVVNNAGIAVNKSVEDTTT
EEWRKLLSVNLDGVFFGTRLGIQAMK-X2-GLGASIINMSSI
EGFVGDPTLGAYNASKGAVRIMSKSAALDCALKDYDVRV
NTVHPGYIKTPLVDDLEGAEEMMSQRTKTPMGHIGEPND
IAYICVYLASDETKFATGAEFVVDGGYTAQ
```

ALCOHOL DEHYDROGENASE AND ITS USE FOR THE ENZYMATIC PRODUCTION OF CHIRAL HYDROXY COMPOUNDS

This application is a Divisional of application Ser. No. 08/822,322 filed on Mar. 21, 1987, now U.S. Pat. No. 6,037,158.

FIELD OF THE INVENTION

The present invention concerns new enantioselective alcohol dehydrogenases (ADH) from microorganisms such as Lactobacillus species especially from *Lactobacillus brevis*. The new enzymes are particularly advantageous for the reduction of organic keto compounds to form the corresponding hydroxy compounds, these reductions leading enantioselectively to the corresponding R compounds. The enantiomeric excess in this process which is calculated as $$ee(\%)=(R)\text{-product}-(S)\text{-product}/(R)\text{product}+(S)\text{-product}\times 100$$

is usually more than 95%. S hydroxy compounds were not detectable when using the ADHS according to the invention. Due to their broad substrate spectrum the enzymes according to the invention can be used, for example, to produce chiral alcohols, chiral hydroxy esters (for example α- and β-hydroxy esters) and also hydroxy acids.

Optically active hydroxy compounds are valuable chiral building blocks which are difficult to prepare with classical chemical processes. Hence biotechnological processes are usually considered for the production of chiral compounds either using whole cells of microorganisms or by means of isolated enzymes. As is shown by, e.g. F. Aragozzini et al. (Appl. Microbiol. Biotechnol. (1986) 24, 175–177), processes using whole cells often result in low yields, only a small enantiomeric excess (i.e. low ee values) and long reaction periods so that enzymes which can be used in a purified and concentrated form are more advantageous. In the case of chiral hydroxy compounds such as alcohols, alcohol dehydrogenases which reduce the prochiral compound with the aid of a coenzyme (often NADH or NADPH) may be used. As a rule these reactions are highly enantioselective. The previously available alcohol dehydrogenases (ADH) all lead to S-alcohols; the substrate spectrum for some of these enzymes is relatively narrow (yeast ADH, horse liver ADH). An NADP-dependent alcohol dehydrogenase from *Lactobacillus kefir* is described in DE 40 14 573 C1. The enzyme produces R-alcohols; however, it has turned out this enzyme is relatively unstable; thus purification to form a homogeneous enzyme could only be accomplished with substantial losses (>98%).

SUMMARY OF THE INVENTION

Surprisingly, an R-specific alcohol dehydrogenase with considerably higher stability was found by intensive screening. If one determines the thermal deactivation of this enzyme compared to the most similar previously known ADH enzyme, it turns out that the previously known enzyme is already inactivated by 50% at 45° C. whereas the enzyme according to the invention is only inactivated by 50% at temperatures of about 65° C. In addition the higher thermostability means a higher storage stability and a higher stability under particular reaction conditions.

A R-ADH enzyme of corresponding stability was found in particular in microorganisms of the genus Lactobacillus such as *L. brevis* and the subgroup Betabacterium (group A). Previously no microorganism or organism was known that had a stable R-specific alcohol dehydrogenase. With the aid of an antibody against the *L. kefir* ADH protein it has now been shown that all Lactobacilli of the subgroup Betabacterium (group A) produce a protein that reacts with the antibody. Particularly good enzymatic activity is detectable in *Lactobacillus brevis*. Other strains of this group also produce an enzyme which, in principle, is suitable for such reactions even if they exhibit a somewhat lower activity under the given culture and test conditions. In contrast, Lactobacilli of other subgroups (Thermobacterium IA, Streptobacterium IB, Betabacterium group B) exhibit neither a reaction in the antibody test nor do they have an appropriate enzymatic activity.

It is possible to purify the stable enzyme obtainable from *L. brevis* to homogeneity. Data for the protein sequence were determined using the purified enzyme.

The biochemical characterizations that were carried out showed further differences the enzymes of the invention and previously known enzymes. These differences include relative activities towards ketones. The stability of the ADHS according to the invention shown maximum stability at a pH value of about 9.0. In addition the enzymes show good stability at about pH 5.5. This is true example, in a 50 mM MES buffer (MES=2-morpholinoethane sulfonic acid). In the same buffer system the enzyme according to the invention still retains activity of over 95% after about 30 minutes at a temperature between 25° C. and 60° C. The enzyme has a stability maximum at ca. 40° C. In addition the enzyme has an activity maximum at ca. 50° C.

Furthermore the enzyme according to the invention ADH enzymes. For example the N-terminal end has five amino acid substitutions over a total length of 38 amino acids (AA), i.e., an AA difference of over 12%. Hence all comparisons demonstrate that it is advantageous to use the alcohol dehydrogenases according to the invention especially those for *Lactobacillus brevis* for corresponding applications.

A further object of the invention involves isolation of the enzyme according to the invention from suitable microorganisms. Good enzyme yields were achieved with a strain of *Lactobacillus brevis* which was deposited on the 06.06.1972 under the number DSM 20054 at the "Deutsche Sammlung von Mikroorganismen und Zellkulturen", Braunschweig and is freely available.

The process for the isolation and purification of the ADH enzyme proceeds essentially via the following process steps: disruption of the cultured cells, such is by glass beads, carrying out hydrophobic chromatography or interaction chromatography and by anion exchange and affinity chromatography. In particular it has proven to be advantageous when all homogenization and elution buffers contain from about 0.5 to about 5 mM magnesium. In this connection a $Mg^{2+}$ concentration of about 1 mM has proven to be particularly advantageous. In this manner an enzyme is obtained which has a specific activity of at least 400 U/mg and in many cases up to 500 U/mg.

In addition the enzyme according to the invention can be produced by remombinant processes i.e. by expressing an appropriate DNA molecule coding for the enzyme in a suitable prokaryotic or eukaryotic strain. In particular a system which is based on an ADH structural gene from *Lactobacillus brevis* transformed into *Escherichia coli* is suitable.

A further subject matter of the invention is a process for the enantioselective reduction of organic keto compounds according to the general formula (I)

(I)

in which $R^1$ and $R^2$ are different or identical, and may be hydrogen, straight-chained or branched alkyl or alkenyl group, an aryl or arylenyl group each group containing of 1 to 20 C atoms which maybe substituted by one or several halogen atoms, nitro, hydroxyl or alkoxy residues, the alkoxy residues having 1 to 20 C atoms, an optionally substituted nitrogen, oxygen or sulphur heterocycle moiety, or may be an optionally substituted polycondensed saturated and/or unsaturated aromatic residue said reaction comprising a keto compound or an appropriate mixture with a microbial alcohol dehydrogenase according to the invention. In this case the enzyme may be used, as may a culture of microorganisms which produce this enzyme or cells containing the enzyme. The reaction is preferably carried out in an aqueous buffer such as potassium phosphate, Tris/HCl or triethanolamine (TEA) buffer, in the presence of magnesium ions, at a pH value of 5 to 10 preferably pH 6 to 9 and at a temperature of 10° C. to 70° C. preferably of 30° C. to 60° C. In addition, an appropriate coenzyme such as NAD(P)H and a suitable agent for the regeneration of oxidized coenzyme such as, isopropanol may be present in the reaction mixture. When an adequate conversion such as a 50% conversion has been achieved, the reaction is terminated, preferably by direct extraction preferably in chloroform. However, the reaction can also be terminated by lowering the pH value, by heating or by adding a suitable enzyme inhibitor. Subsequently, the enantiomerically pure R-hydroxy compound that is obtained is extracted with an organic solvent that is immiscible with water and separated from non-converted keto compounds or other starting compounds or components by known processes of chromatography or distillation. It is expedient to determine the enantiomeric purity by means of and/or on a chiral column material or by means of a polarimeter. The process according to the invention has proven to be especially suitable for the reduction of ketones, keto esters such as α, β or γ ketone esters, and cyclic aryl and alkyl esters preferably those with residues substituted by halogen or alkyl. Particularly good results were achieved for of acetophenone derivatives, methylcyclohexanones, certain diketones such as 2,4-pentanedione, various acetic acid esters and alkyl esters such as ethyl pyruvate.

An object matter of the invention is a process for the production of an enantioselective hydroxy compound according to the general formula (II)

(II)

in which $R^1$ and $R^2$ as are defined, supra is characterized in that a racemic mixture of an organic hydroxy compound is treated with a microbial alcohol dehydrogenase according to the invention or cells containing the ADH, in an aqueous buffer, at a pH value of 5 to 10, preferably pH 6 to 9 and a temperature of 10° C. to 70° C. preferably of 30° C. to 60° C. followed by isolation of the enantiomerically pure S-hydroxy compound obtained is isolated. Otherwise the conditions mentioned above or those known to a person skilled in the art for such reactions apply.

The ADH according to the invention which can be used for the above described reactions either as completely or partially purified enzymes or enzymes present in cells. In this connection the cells can be present in a native, permeabilized or lysed form.

The invention is elucidated in more detail in the following examples:

EXAMPLE 1

Screening for R-Alcohol Dehydrogenases Among Strains of the Genus Lactobacillus

The genus Lactobacillus is divided taxonomically into three subgroups on the basis of physiological characteristics: Thermobacterium, Streptobacterium and Betabacterium, the latter being divided again into the two subgroups A and B. Type strains of all subgroups were tested with an antibody against the alcohol dehydrogenase from *Lactobacillus kefir* to determine whether they react with the antibody. Surprisingly all tested strains of the subgroup A of Betabacterium exhibited reactivity whereas all other strains were inactive. Crude extracts of the strains of subgroup A of Betabacterium were then tested in an enzyme test to determine to what extent enzymatic activity was also present. The results are summarized in Table 1. This shows that under the stated culture and test conditions several strains of this subgroup exhibited no or only a weak enzyme activity although the antibody test was positive. However, it was remarkable that there was particularly high enzyme activity of ADH in samples of *Lactobacillus brevis*.

TABLE 1

Occurrence of R-alcohol dehydrogenase in strains of the genus Lactobacillus

| Strain | Reactivity in the antibody test | Enzyme activity (acetophenone reduction) [U/ml] |
| --- | --- | --- |
| Thermobacterium | | |
| L. acidophilus | 0 | 0 |
| L. helveticus | 0 | 0 |
| L. bulgaricus | 0 | 0 |
| L. delbrueckii | 0 | 0 |
| L. salivarius | 0 | 0 |
| Streptobacterium: | | |
| L. casei | 0 | 0 |
| L. plantarum | 0 | 0 |
| L. alimentarius | 0 | 0 |
| L. curvatus | 0 | 0 |
| L. coryneformis | 0 | 0 |
| L. farciminis | 0 | 0 |
| Betabacterium group A: | | |
| L. kefir | + | 87.0 |
| L. brevis | + | 93.0 |
| L. cellobiosus | + | 0.9 |
| L. fermentum | + | 0.2 |
| L. viridescens | + | 0.2 |
| L. confusus | + | 0.3 |
| L. buchneri | 0 | 0.8 |
| Betabacterium group B: | | |
| L. hilgardii | 0 | 0 |
| L. fructivorans | 0 | 0 |

EXAMPLE 2

Isolation and Purification of Alcohol Dehydrogenase From *Lactobacillus brevis*

A. Culture of *Lactobacillus brevis*

In order to obtain the enzyme *Lactobacillus brevis* was cultured in the following medium (quantities g/L): glucose (20), yeast extract (5), tryptone (10), meat extract (5), di-ammonium hydrogen citrate (2), sodium acetate (5), magnesium sulfate (0.1), manganese sulfate (0.05), di-potassium hydrogen phosphate (2).

The solution was filled up to 1 l and the pH value was adjusted to 6.5, subsequently the medium was sterilized for 10 minutes at 121° C. (2 bar). The strain was cultured at 30° C. without further oxygen supply or pH regulation.

After sterilization and thermostatting at 30° C. the with a 4% preculture ($OD_{660}$ 0.35). The time course of the cell growth and the enzyme activity was determined for this preparation by taking samples at particular time points. These were then examined for $OD_{660}$, fresh weight and enzyme activity after disruption of the cells. The activity of the alcohol dehydrogenase from *L. brevis* exhibits its maximum activity value after reaching the stationary phase of growth which is maintained only for 1.5 h.

The organism was cultured under the same conditions on a 220 l scale, 700 g cell mass was obtained by centrifugation after 13 h at a pH value of 5.3 and an $OD_{660}$ of 2.2. The cell mass can be stored at −20° C. without there being a measurable loss in activity over several months. FIG. 1 shows the growth (represented as optical density) and the formation of enzyme (U/G cells and U/mg protein) in relation to the fermentation time.

B. Enzyme Isolation (Crude Extract Production)

The enzyme was released from the cells by wet-grinding with the aid of glass beads (0.3 mm), but can also be achieved by any other method for disrupting bacterial cells. The bacterial mass is diluted to a 40% suspension with 0.1 M acetate buffer pH 4.0+1 mM $MgCl_2$ supplemented with an antifoaming agent (polypropylene glycol). This was subjected to a 20 minute disruption while cooling continuously in a disintegrator (IMA Co.) at 4000 rpm with addition of glass beads in a ratio of 1:2. 8 g bacteria yielded 10 ml crude extract with a volume activity of 40 U/ml and a protein content of ca. 3 mg/ml. The enzyme reagent contains 970 µl triethanolamine buffer (100 mM; pH 7.0; containing 11 mM acetophenone), 20 µl NADPH (final concentration 0.19 mM) and enzyme solution.

Definition of the enzyme units: 1 U corresponds to the amount of enzyme that is required to convert 1 µmol substrate (acetophenone) per 1 min.

C. Purification of the Alcohol Dehydrogenase From *Lactobacillus brevis*

The enzyme can be purified to homogeneity by hydrophobic interaction chromatography with subsequent anion exchange chromatography and affinity chromatography. In this case it is advisable to add ca. 1 mM $Mg^{2+}$ ions to all buffers. Withdrawal of these ions can irreversibly damage the enzyme.

1. Hydrophobic Interaction Chromatography 5 ml of a crude extract (corresponding to example 2 B) were rebuffered in 50 mM triethanolamine buffer pH 7.0 containing 1 mM $MgCl_2$ and 0.6M $(NH_4)_2SO_4$ by means of small gel filtration columns (PD10, Pharmacia) and applied to a phenyl-Sepharose CL-6B (Pharmacia Co., Freiburg, Germany). The column was equilibrated with 50 mM triethanolamine buffer pH 7.0, 1 mM $MgCl_2$ and 0.6M $(NH_4)_2SO_4$. After the application and rinsing of the column with the equilibration buffer the enzyme was eluted with a decreasing linear salt gradient (6 to 0M $(NH_4)_2SO_4$, flow 1 ml/min) at 0.36M $(NH_4)_2SO_4$. The active fractions are pooled and adjusted to a concentration of 1.2M $(NH_4)_2SO_4$. This protein solution was applied to an octyl-Sepharose column which had been equilibrated with 50 mM triethanolamine buffer pH 7.0, 1 mM $MgCl_2$ and 1.2M $(NH_4)_2SO4$. After applying the protein solution and subsequently rinsing the column, the enzyme was eluted with a decreasing linear salt gradient (1.2 to 0M $(NH_4)_2SO_4$, flow 1 ml/min) at 1.0M $(NH_4)_2SO_4$. The purification achieved is summarized in Table 2 which follows 3, infra.

2. Anion Exchange Chromatography

The fractions with the highest activity from the last column used above were rebuffered in 50 mM Tris/HCl buffer pH 9.0 containing 1 mM $MgCl_2$ by means of gel filtration columns (PD10, Pharmacia) and applied to a mono Q-column (flow 1 ml/min; pressure 1.5 MPA; FPLC chromatography system; Pharmacia Co. Freiburg, Germany) which had also been equilibrated in this manner. After the column had been rinsed, the alcohol dehydrogenase was eluted with a linear salt gradient of 0 to 0.6M NaCl, the enzyme electing at 0.36M NaCl.

3. Affinity Chromatography

The active fractions were rebuffered by means of gel filtration columns (PD 10, Pharmacia Co.) which had been equilibrated with 50 mM morpholinoethane sulfonic acid buffer pH 5.5 and 1 mM $MgCl_2$ and applied to a 2',5' AMP-Sepharose column (Pharmacia Co.) which had also been equilibrated in this manner. Subsequently it was rinsed with 100 mM NaCl dissolved in the same buffer, and then it was it is eluted with a linear NADP gradient of 0 to 10 mM NADP. The dehydrogenase elutes at 3.33 mM NADP. The chromatography was carried out at a flow rate of 0.25 ml/min. The complete purification of the enzyme is summarized in Table 2.

TABLE 2

Purification of the alcohol dehydrogenase from *Lactobacillus brevis*

| Purification step | Activity [U/mg] | spec.act. [U/mg] | Yield [%] |
|---|---|---|---|
| crude extract | 40.8 | 14.78 | 100 |
| phenyl-Sepharose | 17.21 | 45.23 | 42 |
| octyl-Sepharose | 4.6 | 92 | 8 |
| Mono Q | 2.47 | 183 | 4 |
| 2',5'-AMP-Seph. | 11.74 | 489 | 3 |

D. Purification of the Alcohol Dehydroaenase From *Lactobacillus kefir*

*Lactobacillus kefir* has an intracellular NADP-dependent alcohol dehydrogenase (DE 40 14 573 C1) some of whose biochemical properties (production of R-alcohols, coenzyme specificity) are similar to those of the alcohol dehydrogenase from *Lactobacillus brevis*. In order to demonstrate the differences between both enzymes and to show the advantages of the enzyme from *L. brevis*, the alcohol dehydrogenase from *L. kefir* was purified to homogeneity analogously to the *L. brevis* enzyme and during the course of the characterization the *L. brevis* enzyme was tested in comparison (e.g. temperature stability, N-terminal amino acid sequence). The culture of *Lactobacillus kefir*, the enzyme isolation and the purification to a homogeneous enzyme were carried out as described in Example 2A)–2C) for *L. brevis*. Table 3 summarizes the purification of the *L. kefir* enzyme.

TABLE 3

Purification of the alcohol dehydrogenase from *Lactobacillus kefir*

| Purification step | Activity [U/mg] | spec.act. [U/mg] | Yield [%] |
|---|---|---|---|
| crude extract | 57.5 | 9.15 | 100 |
| pheny-Sepharose | 90.0 | 49 | 31 |
| octyl-Sepharose | 7.5 | 100 | 26 |
| Mono Q | 17.5 | 206 | 23 |
| 2',5'-AMP-Seph. | 48.8 | 174 | 8.5 |

Example 2 of the isolation and purification of the ADH from *L. brevis* shows that this enzyme has to some extent similar protein and chemical properties to the *L. kefir* enzyme. Both enzymes, for example, require $Mg^{2+}$ ions in order to avoid irreversible damage. However, the following differences were observed:

1. The ADH enzymes from *L. brevis* and *L. kefir* are detached by significantly different salt concentrations after binding to an ion exchanger material (in this case MonoQ). This difference in binding strength indicates differences in the amino acid composition with regard to the charged amino acids. This could be confirmed by the sequencing described below.
2. The yield of purified, enzymatically active protein is considerably higher for the *L. brevis* enzyme which indicates a more stable enzyme.

EXAMPLE 3

Biochemical Characterization of the Alcohol Dehydrogenase From *Lactobacillus brevis*

A. pH Stability

The dependence of the activity of the enzyme when stored in buffers with various pH values was examined in the range of pH 4 to 11. Depending on the buffer capacity various buffers in the pH range of 4 to 11 were prepared and the homogeneous enzyme was incubated therein for 30 minutes. 1 µl thereof was removed and added to the normal reagent mixture of 970 µl triethanolamine buffer (100 mM; pH 7.0 containing 11 mM acetophenone) and 20 µl NADPH (final concentration 0.19 mM). The reaction was monitored for 1 minute at 30° C. and 340 nm. This showed two maxima of pH stability, a smaller one at pH 5.5 and a larger one at pH 9.0. The stability is shown in Table 4.

TABLE 4 pH stability of the alcohol dehydrogenase

| pH Value | Buffer | Activity [U/ml] |
|---|---|---|
| 4.0 | Na acetate/acetic acid | 6.86 |
| 4.5 | Na acetate/acetic acid | 6.22 |
| 5.0 | MES / NaOH | 7.04 |
| 5.5 | MES / MaOH | 8.73 |
| 6.0 | triethanolamine/NaOH | 5.58 |
| 6.5 | triethanolamine/NaOH | 5.80 |
| 7.0 | triethanolamine/NaOH | 6.57 |
| 7.5 | Tris/HCl | 5.04 |
| 8.0 | Tris/HCl | 3.83 |
| 8.5 | Tris/HCl | 8.42 |
| 9.0 | Tris/HCl | 17.11 |
| 10.0 | glycine/NaOH | 1.25 |
| 11.0 | glycine/NaOH | 2.43 |

B. Temperature Stability

The temperature stability in the range of 25 to 70° C. was determined in an analogous manner to that described under A. The homogeneous enzyme solution was subjected for 30 min to the recited temperatures and subsequently measured directly at 30° C. with the above test mixture. The alcohol dehydrogenase is stable at a temperature range between about 25° and about 60° C. for the stated time period (cf. Table 5), it exhibits maximum stability at 40° C. In contrast the ADH from *L. kefir* is only stable up to 40° C. with a maximum at 37° C., afterwards the activity decreases rapidly. The maximum for this enzyme is at 37° C.

TABLE 5

Temperature stability of the alcohol dehydrogenase from *L. brevis*

| *L. brevis* temperature [° C.] | *L. brevis* act. [U/ml] | *L. kefir* temperature [° C.] | *L. kefir* act. [U/ml] |
|---|---|---|---|
| 25 | 9.43 | 25 | 36.5 |
| 30 | 8.74 | 30 | 30.2 |
| 37 | 12.06 | 37 | 35.8 |
| 40 | 12.15 | 40 | 32 |
| 42 | 11.16 | 45 | 26.2 |
| 45 | 10.81 | 50 | 2.4 |
| 47 | 8.23 | 55 | 0 |
| 50 | 8.37 | | |
| 60 | 8.51 | | |
| 70 | 0.56 | | |

C. Temperature Optimum

In order to determine the optimal test temperature the enzyme activity was measured between 25 and 70° C. The test mixture corresponded to the standard concentrations of acetophenone and NADPH and each was incubated for 5 min at the stated temperatures. The enzyme has its optimal test temperature at 50° C. as shown in Table 6. In contrast the alcohol dehydrogenase from *L. kefir* has an optimum at 37° C. and the activity decreases rapidly at higher test temperatures than 45° C. (Table 5).

TABLE 6

Temperature optimum for the activity of the alcohol dehydrogenase from *Lactobacillus brevis* (compared to the alcohol dehydrogenase from *Lactobacillus kefir*).

| *L. brevis* temperature [° C.] | *L. brevis* act. [U/ml] | *L. kefir* temperature [° C.] | *L. kefir* act. [U/ml] |
|---|---|---|---|
| 25 | 10.31 | 20 | 28.0 |
| 30 | 9.66 | 25 | 28.2 |
| 37 | 9.76 | 30 | 35.2 |
| 40 | 17.78 | 35 | 36.2 |
| 42 | 16.93 | 40 | 34.4 |
| 45 | 18.06 | 45 | 35.4 |
| 47 | 19.13 | 50 | 26.0 |
| 50 | 31.46 | 55 | 3.0 |
| 55 | 24.48 | 60 | 0 |
| 60 | 23.69 | | |
| 65 | 1.98 | | |
| 70 | 0.58 | | |

D. Substrate Spectrum of the Alcohol Dehydrogenase

A series of other ketones and keto esters were used instead of acetophenone and it was tested whether these can be reduced by enzyme catalysis.

The following test mixture was used for this:

970 µl triethanolamine buffer (50 mM; pH 7.0, containing 10 mM keto compound)

20 µl NADPH (0.19 mM in the test)

10 µl purified enzyme (see example 2, after affinity chromatography, diluted 1:10)

Some of the ketones were also tested at a concentration of 1 mM in order to verify a possible substrate inhibition at 10 mM. However, it turned out that such an excess inhibition did not occur at a ketone concentration of 10 mM. The activities obtained for the corresponding substrates are stated in Table 7.

For substrates such as p-Cl-acetophenone, methyl-1-naphthyl ketone and methylcyclohexanone it is possible to make a direct comparison on the basis of literature data between the alcohol dehydrogenase from *L. kefir* and that from *L. brevis* (Hummel, W. Appl. Microbiol. Biotechnol. (1990), 34, 15–19). This comparison shows that the ADH according to the invention converts the said compounds with a higher activity; the activities are ca. 50 to 100% higher than those for the ADH from *L. kefir*.

TABLE 7

Substrate spectrum of the alcohol dehydrogenase from *L. brevis*

| Substrate | Activity [U/ml] | Relative act. [%] |
|---|---|---|
| acetophenone | 3.26 | 100 |
| 4-Cl-acetophenone | 6.63 | 203 |
| 3-Cl-acetophenone | 4.80 | 147 |
| 2-Cl-acetophenone | 0.33 | 10 |
| 4-ethylacetophenone | 2.13 | 65 |
| 2-methylcyclohexanone | 6.25 | 192 |
| 2-oxo-4-phenylbutyric acid ethyl ester | 4.60 | 141 |
| 2,4-pentanedione | 4.22 | 130 |
| aceto acetic acid benzyl ester | 4.11 | 126 |
| aceto acetic acid methyl ester | 3.81 | 117 |
| aceto acetic acid ethyl ester | 3.54 | 109 |
| benzylacetone | 3.24 | 99 |
| methyl pyruvate | 3.22 | 98 |
| ethyl pyruvate | 8.10 | 248 |
| 4-Cl-acetic acid ethyl ester | 3.04 | 93 |
| laevulinic acid ethyl ester | 2.99 | 92 |
| 4-acetylbutyric acid ethyl ester | 2.84 | 87 |
| 3-oxo-n-valeric acid ethyl ester | 2.29 | 70 |
| 3-oxo-n-valeric acid methyl ester | 2.26 | 69 |
| ethylbutyryl acetate | 2.21 | 68 |
| acetic acid butyl ester | 2.07 | 64 |
| isobutyrylacetic acid ethyl ester | 1.93 | 59 |
| methyl-1-naphthyl ketone | 1.21 | 37 |
| benzoyl acetic acid ethyl ester | 1.14 | 35 |
| ethyl-2-methylacetoacetate | 0.84 | 26 |
| 1,4-butanediol-diglyceridyl ether | 0.77 | 24 |
| hydroxyacetone | 0.74 | 23 |
| propiophenone | 0.55 | 17 |
| trifluoroacetic acid ethyl ester | 0.50 | 15 |
| cyclohexanone-2-carboxylic acid ethyl ester | 0.41 | 13 |
| ethyl-2-oxo-4-phenyl butyrate | 0.40 | 12 |
| benzylmethyl ketone | 0.36 | 11 |
| 4-acetylbutyric acid | 0.32 | 10 |
| benzaldehyde | 0.30 | 9 |
| ketovaleric acid | 0.27 | 8 |
| cyclohexanone-2-acetic acid ethyl ester | 0.14 | 4 |

The substrate spectrum of the enzyme according to the invention is similar in broadness to that of the *L. kefir* enzyme. Both enzymes convert acetophenone derivatives, 2- and 3-oxoesters, cyclic and open-chained ketones with a high activity and are capable of forming R-alcohols by reduction of ketones.

E. Molecular Weight of the Alcohol Dehydrogenase From *Lactobacillus brevis*

Purified alcohol dehydrogenase from *Lactobacillus brevis* was applied to a gel filtration column Superdex G-200 (Pharmacia Co., Freiburg). The molecular weight was determined according to a calibration curve which was obtained with proteins of known molecular weight. The buffer in the gel filtration had the usual pH value for the purification of 7.0 (100 mM TEA, pH 7.0, 0.2M NaCl, 1 mM $MgCl_2$). Under these conditions a molecular weight of ca. 104 kD was determined for the *L. brevis* ADH which corresponded to that of the *L. kefir* ADH. Moreover both enzymes are composed of four subunits.

F. Determination of the N-Terminal Sequence of the Alcohol Dehydroaenase

The N-terminal sequence was determined with a Pulsed Liquid Sequencer Model 477A using an on-line HPLC model 120A from the Applied Biosystems/U.S.A. Co. and compared with the N-terminal sequence of the alcohol dehydrogenase from *L. kefir*.
S-N-R-L-D-G-K-V-A-I-V-T-G-G-T-L-G-I-G-L-A-I-A-T-K-F-V-E-E-G-A-K-V-M-I-T-T-R (SEQ ID NO:1)

In comparison to the sequence from *L. kefir* the following five amino acid substitutions were recorded in the first 38 amino acids (AA):

pos. 1 Thr by Ser (no difference in the chemical behaviour of the AA);

pos. 2 Asp by Asn (acidic, charged AA is substituted by an uncharged AA);

pos. 5 Lys by Asp (basic AA is substituted by an acidic AA);

pos. 24 Asp by Thr (acidic AA substituted by hydrophilic AA);

pos. 34 Val by Met (hydrophobic AA substituted by an AA containing sulphur).

In four of the five cases amino acid substitutions are present which produce opposite polarity properties at these positions in the enzyme.

EXAMPLE 4

Determination of Amino Acid Partial Sequences After Cleaving the Enzyme

Homogeneous alcohol dehydrogenase from Lactobacillus brevis was subjected to cleavage with endoproteinase Lys-C protease (Boehringer Mannheim, 476 986). For this the protein had to be previously denatured and carboxy-methylated before hand. The ADH sample was taken up directly in 60 μl guanidinium buffer pH 8.5 [2 mg/ml] and incubated for 30 minutes at room temperature. After the incubation was completed, 1/10 volumes of a 111 mM DTT solution was added and incubated again for 30 min at 37° C. Finally 1/10 volumes of a 360 mM iodoacetic acid solution were added and the sample was incubated in darkness for 30 min at 37° C. The reaction was terminated with β-mercaptoethanol. After rebuffering in a buffer containing urea (2M), 1% (final concentration) Triton X-100 (reduced) and 4.6 μg Lys-C protease (1/25 of the protein amount [w/w]) were added and the mixture was incubated overnight at 37° C. After at least 16–18 h the reaction was terminated by addition of 1/10 volumes 10% TFA. Three times 2×150 μl and finally 1×100 μl of the mixture were injected into the HPLC column. Each peak containing protein was collected separately and, after comparing the individual runs, the same peaks were pooled and concentrated in a vacuum centrifuge. These samples (a total of 18) were then used directly for sequencing.

Sequence data (only the most important data for fractions with unequivocal complete sequence information are listed):

The protein in peak fraction number 3 has the following sequence V-M-I-T-G-R-H-S-D-V-G-E-K (SEQ ID NO:2) and is thus linked directly to the N-terminal end.

The sequences of the protein fractions number 5 (D-Y-D-V-R-V-N-T-V-H-P-G-Y-I-K, SEQ ID NO:3)) and number 6 could also be determined.

In the case of the latter F-A-T-G-S-E-F-V-V-D-G-G-Y-T-A-Q (SEQ ID NO:4) it corresponds to the C-terminal end of the monomer of the ADH from *Lactobacillus brevis*.

The sequences of the remaining 12 fractions are not listed here. However, it was possible to confirm all partial sequences by appropriate cloning.

A corresponding experiment for cleaving purified ADH from *L. kefir* with protease lys-C was successful. When the peptides were separated by means of HPLC this yielded a cleavage pattern with a high degree of similarity to that obtained for the cleavage of the enzyme from *L-brevis*. From this cleavage it was possible, after sequencing the peptide cleavage fragments to obtain almost the complete amino acid sequence of the *L. kefir* enzyme. When the identified sequence fragments were compared with the sequence of the ADH from *L. brevis* (see FIG. 2) it turned out that the partial fragments of the *L. kefir* sequence essentially corresponded to the *L. brevis* sequence but too decisive partial fragments are absent in the *L. kefir* sequence. These partial fragments are labelled in FIG. 2 by $X_{26}$ i.e. a partial fragment which must comprise 26 amino acids in order to achieve a matching with the *L. brevis* sequence and labelled with $X_2$ for a partial fragment comprising two amino acids.

Figure 2:
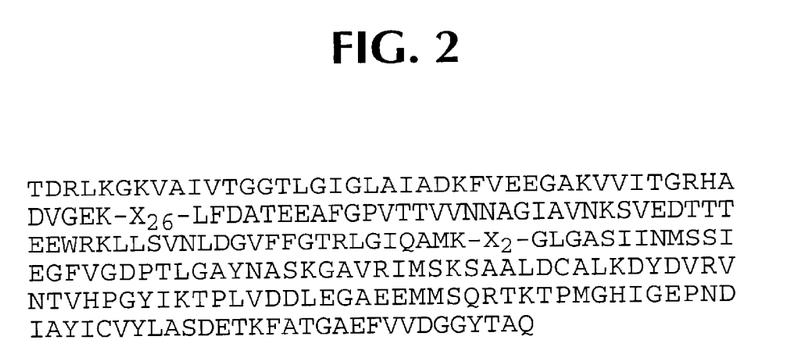

A comparison of the sequence of the ADHs from *L. brevis* and *L. kefir* shows that—apart from the missing partial fragments $X_{26}$ and $X_2$—18 amino acids i.e. ca. 10% are different.

EXAMPLE 5

Cloning of the Enzyme

A. Preparation of Genomic DNA From *Lactobacillus brevis*

Cells of *Lactobacillus brevis* were washed with 50 ml high TE buffer (25 mM Tris, 10 mM EDTA pH 8.0) and centrifuged at 6000 rpm. The pellet was resuspended in 10 ml TE (25 mM Tris, 10 mM EDTA pH 8.0) and incubated for 1.5 h at 37° C. with addition of 100 µl lysozyme (100 mg/ml). Subsequently the cell protein was denatured and the RNA was degraded overnight at 50° C. by addition of 340 µl 30% sodium lauryl sarcosine, 100 µl Qiagen protease (Hilden; 20 mg/ml) and 25 µl RNAse A (40 mg/ml) to the lysed cells. In the next step the DNA from the cell lysate was separated from the other cell contents by phenyl precipitations. (To do this first pure phenol (saturated with TE), then phenol/IAA/CHCl$_3$ (25:24:1) (IAA=isoamyl alcohol) and finally IAA/CHCl$_3$ (24:1) were added in a volume ratio of 1:1 to the aqueous phase). The combined aqueous phases were then mixed for ca. 5 minutes by gentle swirling and then separated by centrifugation at 20000 rpm. The last aqueous upper phase was admixed with 0.0625 volumes 8 M LiCl and then carefully covered with a layer of two volume parts cold ethanol (100%). The genomic DNA that precipitated at the boundary layer was wound onto a Pasteur pipette and washed twice with cold 70% ethanol. After drying in a vacuum centrifuge, the DNA was taken up in 2 ml TE (10 mM Tris, 1 mM EDTA) pH 8.0. In order to check the degree of purity of the isolated DNA the solution was diluted 1:50 and the 260:280 nm quotient was determined photometrically as 2.0. Hence protein impurities could be ruled out. The concentration of the DNA from the gel was determined to be 70 ng/µl, 140 µg genomic DNA was isolated from 3 g of cells.

B. Oligonucleotides as 5' and 3' Primers for the PCR (Polymerase Chain Reaction)

The N-terminal and C-terminal end of the protein sequence of the ADH from *L. brevis* could be determined on the basis of enzymatic peptide cleavages (see example 4). Primers for the PCR were synthesized using this information. In doing so the known preferences for particular codons in Lactobacilli were taken into account. The codon ATG (Met) was placed in front of each 5' primer as a start codon, which is lacking for the protein sequence, and 2 stop codons were placed behind each 3' primer for the secure termination of the translation. The primer constructs are listed in the following (the variable nucleic acids are shown in parentheses which were incorporated as an alternative to the nucleic acid before the parentheses so that the primer actually used is a mixture of the resulting combinations):

5' primer 5'LB:
   5'ATG-TCA-AAC-CGT-TTA(G)-GAT-GGT(C)-AAG-GTT(A)-GCT(A)-ATT(C)-3' (SEQ ID NO:5)

3' primer 3'LB:
   5'CTA-CTA-TTG-A(T)GC-AGT-GTA-A(G)CC-A(G)CC-ATC-A(T)AC-A(T)AC-GAA-3' (SEQ ID NO: 6)

The synthesized primers were eluted with cold NH$_3$ from the columns. This NH$_3$ solution was incubated for 1 h at 70° C. and subsequently shaken out with 1 ml butanol. The samples were centrifuged for 2 minutes at 14000 rpm and the supernatant formed was decanted. The samples were placed for 5 min in a vacuum centrifuge to dry and the pellet was taken up in 500 µl H$_2$O. The primers were used at a concentration of 100 pmol/µl.

C. PCR (Polymerase Chain Reaction) With the Genomic DNA From *L. brevis*

In the following the template concentration (genomic DNA) was varied, all other parameters were kept constant. 52° C. was selected as the annealing temperature.

TABLE 8

| | | | PCR mixture | | | | |
|---|---|---|---|---|---|---|---|
| Mixture | Template [ng] | 5' primer [pmol] | 3' primer [pmol] | dNTP [nM] | buffer [10×] | Taq [U] | H$_2$O [µl] |
| 1 | 700 | 100 | 100 | 1.6 | 10 µl | 2.5 | 61.5 |
| 2 | 70 | 100 | 100 | 1.6 | 10 µl | 2.5 | 70.5 |

The respective mixtures had a volume of 100 µl. The molecular data are to be understood as final concentrations. The template and the Tag polymerase were added to the total mixture in the amounts listed in Table 8. The buffer was present in a 10-fold concentration. The PCR was carried out overnight for 25 cycles.

For the analytical work 10% of the mixture (volume portion) was applied to a 1% agarose gel and electrophoretically separated at a constant 100 V. The PCR shows a substantial amplification of a DNA fragment of ca. 750 bp. The signal lies between the marker bands of 697 bp and 925 bp but it is nearer to 697 bp. With a determination of the molecular weight of the monomer of ADH of 27 kD (245 AA) by SDS-PAGE, there is a good agreement in this case of the amino acid length of the ADH protein and of the base pair length for the sought-after gene.

D. Purification of the PCR Products

500 µl buffer PB was added by pipette to 100 µl PCR solution and directly applied to a Quiaquick® column (without equilibration). The DNA was bound to the column by centrifugation (1 min, 14000 rpm), the eluant was discarded. The column was washed with 750 µl buffer PE by centrifugation (1 min, 14000 rpm) and the eluant was discarded. The column was again briefly centrifuged in order to remove remnants of the ethanol in the PE buffer. Subsequently the column was eluted by centrifugation (1 min, 14000 rpm) by addition of 50 µl 2 mM Tris/HCl pH 8.0. For control purposes 1 μl of the eluate was applied to an analytical 0.8% agarose gel and electrophoretically separated at a constant 60 V. The concentration determination yielded 70 ng/μl for PCR3/1 and 90 ng/μl for PCR3/2. PCR3/2 was processed further, PCR3/1 was stored at −20° C. PCR3/2 was concentrated to 16 μl in a speed vac and used directly for a blunting/kinase reaction (16 μl PCR, 1 μl Klenow fragment, 2 μl 10× buffer, 1 μl polynucleotide kinase; incubated for 30 min at 37° C.). The reaction mixture was applied directly to a preparative 0.8% agarose gel (2 h, 80 V constant). The visible band at 750 bp was cut out of the gel and isolated from the gel by means of Jetsorb® (Genomed, Bad Oeynhausen). The plasmid DNA was eluted from the Jetsorb material with 50 μl 2 mM Tris/HCl pH 8.0. This solution was concentrated to 9 μl with the aid of a vacuum centrifuge. 1 μl of this was used for an analytical agarose gel.

The concentration of the PCR fragment in the gel (150 ng/μl) yielded a total concentration of DNA of 1.2 μg. This sample was used in the ligase mixture of the Sureclone kit.

E. DNA Isolation From the Gel

300 μl buffer A1 and 10 μl of the Jetsorb suspension were mixed per 100 mg gel material and incubated for 15 min at 50° C. During this the solution was mixed again from time to time in order to ensure complete binding to the Jetsorb material. Subsequently the suspension was centrifuged for 30 sec. at 11000 rpm, the supernatant was discarded, the pellet was resuspended in 300 μl buffer A2 and again centrifuged at 11000 rpm. This step was completely repeated and subsequently the supernatant was carefully removed by pipette and the pellet was dried for 5 min at 50° C. Then the pellet was resuspended in 30 μl 2 mM Tris/HCl pH 8.0 and incubated for 5 min. at 50° C. After the centrifugation (11000 rpm, 30 sec) was completed, the supernatant was collected and the pellet was again resuspended in 20 μl 2 mM Tris/HCl pH 8.0 and treated further as described above. The resulting supernatants were pooled and concentrated to 18 μl in a Speed vac. 1 μl of this was applied to an analytical agarose gel. The concentration determination by means of this gel yielded a DNA concentration of 10 ng/μl i.e. a total concentration of 160 ng.

F. Ligation

7 μl PCR (1 μg), 1 μl pUC18 vector (50 ng), 1 μl DTT, 10 μl two-times ligase buffer and 1 μl ligase were used. 3 μl was removed from this mixture and used in a new ligase mixture in order to lower the PCR fragment concentration. A second mixture corresponds to the composition of the first mixture (ratio of 1:20 vector:PCR) apart from the PCR-DNA concentration (157 ng, i.e. a ratio of 1:3 vector:PCR). Both mixtures were incubated for 1.5 h at 16° C. and subsequently 100 μl competent cells (*Escherichia coli* XL 1 Blue) were in each case transformed therewith. 1 μl of the ligase mixture 1 and 4 μl of the ligase mixture 2 were added by pipette to the competent cells. 300 μl of the cell suspension in each case was plated out on $LB_{amp}$-agar plates (LB=casein peptone/yeast extract; pH 7.5).

Grown colonies were inoculated and cultured overnight at 37° C. in 4 ml liquid culture ($LB_{amp}$-medium). 2 ml of this cell suspension was in each case used for the plasmid preparation. The plasmid DNA was directly precipitated from the cell-free solution using 0.7 volume parts isopropanol, washed with cold 70% ethanol, dried in a vacuum centrifuge and taken up in 10 μl 2 mM Tris/HCl buffer (pH 8.0). A restriction digestion was prepared from this plasmid preparation using EcoR1 and HindIII (1 U/μl enzyme, 6 μl plasmid DNA, 37° C., 1 h). The complete digest was applied to a 0.8% agarose gel, electrophoretically separated for 2 hours at a constant 80 V (detection of the 750 bp insert) and the plasmids were optionally afterwards used for the sequencing.

G. Plasmid Preparation 4 ml of the liquid culture were centrifuged for 5 min at 5000 rpm and the pellet was resuspended in 300 μl buffer P1. 300 μl buffer P2 was added to this suspension and the cell suspension was incubated for 5 min at room temperature. Afterwards 300 μl cold P3 buffer was added to the lysed cells by pipette and incubated for 10 min on ice while swirling several times in order to denature nucleic acids and proteins. The denatured components were removed by centrifugation (11000 rpm, 15 min); the supernatant was directly applied to new 20 tip columns that had been equilibrated with 1 ml QBT buffer. The columns were washed with 4×1 ml QC buffer and subsequently the plasmid DNA was eluted from the columns with 0.8 ml QF buffer. The DNA was precipitated from this solution with 0.7 vol isopropanol after 30 min centrifugation at 14000 rpm. The resulting pellet was washed 2×10 min with 70% ethanol during the centrifugation at 14000 rpm and then dried in a vacuum centrifuge. The DNA was taken up in 10 μl 2 mM Tris/HCl pH 8.0 and for example used for the analyses by means of restriction enzymes.

H. DNA Sequencing of the Plasmids a. Preparation of the Sequence Gel

The sequencing was carried out using the autoread laser fluorescent sequencer kit. The gel had a standard thickness of 0.5 mm. An appropriate glass plate (thickness 0.35 mm) was used at the site of the laser passage. Sequencing gel: 21 g urea (ultra pure), 12 g $H_2O$ (Millipore), 7.5 ml acrylamide (Roth, for the DNA sequencing), 200 μl APS, 45 μl TEMED, 6 ml 10-times TBE. 0.6×TBE (Tris/borate/EDTA buffer corresponding to the Pharmacia instructions) served as the mobile buffer.

b. Sequencing Reaction

5 μl (4 μg) DNA of the plasmids was in each case used per sequencing primer.

5 μl plasmid DNA, 5 μl $H_2O$, 2 μl primer (universal or reversal), 1.5 μl 1 M NaOH were pipetted together and incubated for 5 min at 65° C. in order to denature the DNA. Then the samples were directly transferred to 37° C. and the reaction was neutralized with 1.5 μl 1 M HCl. 2 μl annealing buffer was added, briefly centrifuged (15 sec, 14000 rpm) and incubated for 10 min at 37° C. and subsequently for a further 10 min at room temperature. After centrifugation was completed 1 μl extension buffer and 3.5 μl dimethyl sulfoxide were admixed-with the preparation and 2 μl of the T7 polymerase diluted with the enzyme dilution buffer was added by pipette per mixture. 5.2 μl of this solution was directly pipetted into a plate preincubated at 37° C. which contained 4 lanes with 3 μl of the respective NTP mix per plasmid (A, C, G, T, in this order). After 5 min incubation at 37° C. the sequencing reaction was terminated according to Sanger (Sanger, F., Nickler, S., Coulson, A. R. (1977). Proc. Natl. Acad. Sci. U.S.A. 74, 5463–5467) by addition of 6 μl stop mix and the reaction mixture was heated for 2–3 min at 90° C. Then it was cooled on ice in order to prevent renaturation of the strands. 6 μl of this mixture was then directly applied to a sequence gel and the sequencer was started. Of the selected plasmids only plasmid 3/1 had the correct DNA sequence. These data were then translated into the corresponding protein sequence (FIG. 1). The universal primer shows the C-terminal end of the sequence and the reversal primer the N-terminal end (5' coding strand). Hence the insert is placed in the correct orientation. The sequence based on the DNA sequencing shows complete correspondence with the sequence data obtained by protein sequencing.

EXAMPLE 6

A. Construction of the pADH Expression Plasmid

In order to express the alcohol dehydrogenase the structural gene was cloned into the pKK177 expression vector in such a way that the structural gene is inserted in the correct orientation under the control of a suitable promoter that can be induced by IPTG preferably the tac promoter. For this the structural gene for the alcohol dehydrogenase was cut out of the pUC vector containing the ADH gene by means of EcoRI and HindIII, the restriction mixture was separated by agarose gel electrophoresis and the ca. 750 bp large fragment was isolated from the agarose gel. At the same time the expression plasmid pKK177 was cut with EcoRI and HindIII, the restriction mixture was separated by agarose gel electrophoresis and the ca. 2.8 kbp vector fragment was isolated from the agarose gel. The fragments obtained in this way were ligated together as described. The newly formed plasmid was named pADH-1. The correct insertion of the gene was checked by means of restriction analysis and sequencing.

B. Transformation of the Expression Plasmid pADH-1 Into Various *Escherichia coli* Expression Strains Competent cells of various *Escherichia coli* strains preferably *E. coli* B HB101 and *E. coli* K12NM522 were prepared according to the method by Hanahan (J. Mol. Biol. 166 (1983) pp. 557). 200 µl of the cells produced in this way were admixed with 20 ng isolated pADH-1 plasmid DNA. After 30 min incubation on ice this was followed by a heat shock (90 sec at 42° C.). Subsequently the cells were transferred to 1 ml LB medium and incubated for 1 hour at 37° C. for the phenotypic expression. Aliquots of this transformation mixture were plated onto LP plates containing ampicillin as the selection marker and incubated for 15 hours at 37° C.

C. Expression of the Alcohol Dehydrogenase From *Lactobacillus brevis* in *Escherichia coli*

Transformants which have taken up the expression plasmid pADH-1 were picked and individually reinoculated in 3 ml LB liquid medium containing ampicillin and incubated at 37° C. in a roller. The cells were induced with 1 mM IPTG at an optical density (measurement wavelength 550 nm) of 0.5. As a control in each case a clone was also processed containing the expression plasmid but without induction and the respective *E. coli* WT without the expression plasmid but induced with IPTG. 4 hours after the induction and overnight growth an aliquot was taken from each tube which corresponded to an optical density of $OD_{550}$=5. The cells were centrifuged (10 min at 6000 rpm, 4° C.), taken up in 300 µl TE buffer (50 mM Tris-HCl, 50 mM EDTA, pH 8.0) and lysed by means of ultrasound (Branson Sonifire 450/2× 30 sec at level 2 on ice). The soluble proteins were separated from insoluble proteins and cell wall components by means of centrifugation (10 min, 14000 rpm). At this point an aliquot was removed to carry out the activity test. The remaining supernatant was admixed with 50 µl 5×application buffer (60 mM Tris-HCl pH 6.8, 1.2% SDS, 10% glycerol, 0.7M 2-mercaptoethanol, 0.05% bromophenol blue) to prepare for the SDS polyacrylamide gel electrophoresis. The protein pellet (insoluble proteins and cell wall components) was again taken up in 300 µl TE buffer (50 mM Tris-HCl, 50 mM EDTA, pH 8.0) and resuspended by 5 impulses of ultrasound (Branson Sonifire 450). These samples were also admixed with the respective volume of 5×application buffer. Finally all samples were heated for 5 min to 95° C. in order to completely denature the proteins.

D. SDS Polyacrylamide Gel Electrophoresis (SDS-PAGE)

SDS-PAGE was carried out according to the method of U.K. Laemmli (1970, Nature 227, pp. 680–685). Soluble and insoluble protein fractions were separated separately in a 15% separation gel and the protein bands were subsequently stained with Coomassie staining solution (0.2% Coomassie, 30% ethanol, 10% acetic acid).

The alcohol dehydrogenase from *Lactobacillus brevis* of the *E. coli* strains used was exclusively expressed as a soluble protein. It was possible to show this exclusively for the soluble protein fractions based on an additional protein band having the previously determined size of 27 kDA on the SDS-PAGE. This additional protein band was not seen in the controls (non-induced, clone containing plasmid and induced clone which does not contain plasmid) and in samples containing the insoluble protein fraction.

An activity test carried out using the crude extract also showed that the alcohol dehydrogenase was not only expressed in a soluble form but also in an active form.

EXAMPLE 7

Enzyme-Catalysed Production of R-phenylethanol

Purified enzyme (example 2C) and the necessary coenzyme (NADP) were used for the enzyme-catalysed synthesis of (R)-phenylethanol from acetophenone. The oxidized co-enzyme was continuously regenerated by isopropanol which was simultaneously present so that the reaction only required catalytic amounts of coenzyme. In. detail the mixture contained (the final concentrations of the components in the test are listed in brackets): 20 µl NADP (0.05 mM), 7.7 µl isopropanol (0.1M), 0.6 µl acetophenone (5 mM), 921.7 µl triethanolamine buffer (50 mM; pH 7.0, containing 1 mM $MgCl_2$) and 50 µl alcohol dehydrogenase from *Lactobacillus brevis* (4.5 units). This mixture with a total volume of 1 ml was incubated for 24 hours at 30° C., then a sample was analysed by means of gas chromatography. For this 100 µl was removed, shaken out with 100 µl chloroform, the phases were separated by centrifugation and an aliquot was taken from the lower phase (chloroform) for the GC.

The separation conditions for the separation of (R)- and (S)-phenylethanol on a gas chromatograph: stationary phase: Lipodex E, CD column (Macherey and Nagel, Düren), mobile phase: helium, injection volumes: 1 µl detection: FID, temperature: 110° C. Under these conditions the substrate acetophenone is eluted at 10.5 min, (S)-phenylethanol at 13.8 min and (R)-phenylethanol at 14.2 min. The retention values for (S)- and (R)-phenyl-ethanol can be obtained with a commercially available, racemic mixture (Fluka Co. Buchs, Switzerland). After 24 hours more than 95% of the substrate has been converted, the GC chromatogram shows the following values: acetophenone (retention time 10.5 min): area=9.800; (S)-phenylethanol (retention time 13.8 min): area=<500; (R)-phenylethanol (retention time 14.2 min): area=240000.

EXAMPLE 8

Production of Alcohols by Reduction of Ketones With Whole Cells of *Lactobacillus brevis*

In addition ketones can be reduced to chiral alcohols using whole cells of *L. brevis*. In this case NADP does not have to be added since coenzyme that is present intracellularly is utilized. The coenzyme regeneration can be achieved by isopropanol or by metabolizable substrates such as glucose.

Test mixture: 50 mg cells of *L. brevis* (wetweight after centrifugation) is suspended in 860 µl triethanolamine buffer (50 mM; pH 7.50; addition of 1 mM $MgCl^{2+}$) which contains 0.1M glucose and 10 mM acetophenone. Samples are analysed by means of gas chromatography. After 2 h incubation at 30° C. acetophenone is no longer detectable and in its place a corresponding amount of phenylethanol has then formed. Since a quantification by means of GC separation on a chiral stationary phase had been carried out, it was possible to show at the same time that the phenylethanol that forms is of high optical purity but no quantifiable (S)-alcohol could be detected. The optical purity is considerably >95% for (R)-alcohol. This shows that cells of *L. brevis* apparently do not contain a further alcohol dehydrogenase which can interfere with the optical purity of the alcohols formed so that chiral alcohols can also be produced in this way using whole cells.

Legend for FIG. 1
DNA and protein sequence of the recombinant ADH from *L. brevis* in *E. coli* (upper line nucleic acid sequence in each case (SEQ ID NO.7), below the amino acid sequence corresponding to the triplet code (in the single letter code, SEQ ID NO:8)). The sequence starts with methionine which had been inserted via a start codon. This methionine is not found in the corresponding amino acid sequence which had been obtained by sequencing the pure protein (N-terminal end; see example 3F and example 4).

Legend for FIG. 2
Amino acid sequence (SEQ ID NO:9) of the alcohol dehydrogenase from *Lactobacillus kefir* obtained by sequencing peptides after cleaving the enzyme by LysC protease.

We claim:

1. A process for recombinant production of an alcohol dehydrogenase, comprising transferring or transfecting a prokaryotic or eukaryotic cell with a nucleic acid molecule which encodes the protein of SEQ ID NO:8, culturing said cell, expressing said alcohol dehydrogenase, and isolating said alcohol dehydrogenase produced thereby.

2. The process of claim 1 wherein said nucleic acid molecule comprises the nucleotide sequence of SEQ ID NO:7.

3. An isolated nucleic acid molecule from *Lactobacillus brevis* encoding an alcohol dehydrogenase which catalyzes the conversion of acetophenone to R-phenylethanol, wherein said alcohol dehydrogenase retains at least 95% activity after about 30 minutes incubation over a temperature range of about 20° C. to about 60° C.

4. The isolated nucleic acid molecule of claim 3, wherein said alcohol dehydrogenase comprises the amino acid sequence of SEQ ID NO:8.

5. The isolated nucleic acid molecule of claim 3 consisting of the nucleotide sequence set forth in SEQ ID NO:7.

* * * * *

UNITED STATES PATENT AND TRADEMARK OFFICE
CERTIFICATE OF CORRECTION

PATENT NO. : 6,225,099 B1
DATED : May 1, 2001
INVENTOR(S) : Hummel et al.

Page 1 of 1

It is certified that error appears in the above-identified patent and that said Letters Patent is hereby corrected as shown below:

Column 1,
Line 26, after line 26, insert a new line -- BACKGROUND AND PRIOR ART --.

Column 2,
Line 18, after "differences" insert -- of --.
Line 30, after "invention" insert -- have different amino acid sequences as compared to previously known --.

Column 3,
Line 17, after 'ing" insert -- treating --.
Line 40, after "of" insert -- gas chromatography (GC) --.
Line 40, after "and/or" insert -- high performance liquid chromatography (HPLC) --.

Column 5,
Line 15, after "the" insert -- medium was inocullated on a 10 liter scale in a fermenter --.

Column 15,
Line 7, change "tac" to -- Tac --.

Signed and Sealed this

Twenty-ninth Day of January, 2002

Attest:

Attesting Officer

JAMES E. ROGAN
*Director of the United States Patent and Trademark Office*

```
                      SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO: 1:

Ser Asn Arg Leu Asp Gly Lys Val Ala Ile Val Thr Gly Gly Thr
1               5                   10                  15

Leu Gly Ile Gly Leu Ala Ile Ala Thr Lys Phe Val Glu Glu Gly
                20                  25                  30

Ala Lys Val Met Ile Thr Thr Arg
                35

(2) INFORMATION FOR SEQ ID NO: 2:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 2:

Val Met Ile Thr Gly Arg His Ser Asp Val Gly Glu Lys
1               5                   10

(2) INFORMATION FOR SEQ ID NO: 3:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 3:

Asp Tyr Asp Val Arg Val Asn Thr Val His Pro Gly Tyr Ile Lys
1               5                   10                  15
```

(2) INFORMATION FOR SEQ ID NO: 4:

(i) SEQUENCE CHARACTERISTICS:
        (A) LENGTH: 16 amino acids
        (B) TYPE: amino acid
        (D) TOPOLOGY: linear     (ii) MOLECULE TYPE: peptide     (xi) SEQUENCE DESCRIPTION: SEQ ID NO: 4:

```
Phe Ala Thr Gly Ser Glu Phe Val Val Asp Gly Gly Tyr Thr Ala Gln
 1               5                   10                  15
```

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 5:

ATGTCAAACC GTTTRGATGG YAAGGTRGCR ATY                                                      33

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO: 6:

CTACTATTGY GCAGTGTARC CRCCATCYAC YACGAA                                                36

(2) INFORMATION FOR SEQ ID NO: 7:

(i) SEQUENCE CHARACTERISTICS:
        (A) LENGTH: 756 base pairs
        (B) TYPE: nucleic acid
        (C) STRANDEDNESS: double
        (D) TOPOLOGY: linear     (ii) MOLECULE TYPE: DNA (genomic)

(ix) FEATURE:
        (A) NAME/KEY: CDS
        (B) LOCATION:1..756

(xi) SEQUENCE DESCRIPTION: SEQ ID NO: 7:

```
ATG TCT AAC CGT TTG GAT GGT AAG GTA GCA ATC ATT ACA GGT GGT        45
Met Ser Asn Arg Leu Asp Gly Lys Val Ala Ile Ile Thr Gly Gly
 1               5                   10                  15

ACG TTG GGT ATC GGT TTA GCT ATC GCC ACG AAG TTC GTT GAA GAA        90
Thr Leu Gly Ile Gly Leu Ala Ile Ala Thr Lys Phe Val Glu Glu
                20                  25                  30

GGG GCT AAG GTC ATG ATT ACC GGC CGG CAC AGC GAT GTT GGT GAA       135
Gly Ala Lys Val Met Ile Thr Gly Arg His Ser Asp Val Gly Glu
            35                  40                  45

AAA GCA GCT AAG AGT GTC GGC ACT CCT GAT CAG ATT CAA TTT TTC       180
Lys Ala Ala Lys Ser Val Gly Thr Pro Asp Gln Ile Gln Phe Phe
            50                  55                  60

CAA CAT GAT TCT TCC GAT GAA GAC GGC TGG ACG AAA TTA TTC GAT       225
Gln His Asp Ser Ser Asp Glu Asp Gly Trp Thr Lys Leu Phe Asp
```

```
GCA ACG GAA AAA GCC TTT GGC CCA GTT TCT ACA TTA GTT AAT AAC      270
Ala Thr Glu Lys Ala Phe Gly Pro Val Ser Thr Leu Val Asn Asn
                80                  85                  90

GCT GGG ATC GCG GTT AAC AAG AGT GTC GAA GAA ACC ACG ACT GCT      315
Ala Gly Ile Ala Val Asn Lys Ser Val Glu Glu Thr Thr Thr Ala
                95                 100                 105

GAA TGG CGT AAA TTA TTA GCC GTC AAC CTT GAT GGT GTC TTC TTC      360
Glu Trp Arg Lys Leu Leu Ala Val Asn Leu Asp Gly Val Phe Phe
               110                 115                 120

GGT ACC CGA TTA GGG ATT CAA CGG ATG AAG AAC AAA GGC TTA GGG      405
Gly Thr Arg Leu Gly Ile Gln Arg Met Lys Asn Lys Gly Leu Gly
               125                 130                 135

GCT TCC ATC ATC AAC ATG TCT TCG ATC GAA GGC TTT GTG GGT GAT      450
Ala Ser Ile Ile Asn Met Ser Ser Ile Glu Gly Phe Val Gly Asp
               140                 145                 150

CCT AGC TTA GGG GCT TAC AAC GCA TCT AAA GGG GCC GTA CGG ATT      495
Pro Ser Leu Gly Ala Tyr Asn Ala Ser Lys Gly Ala Val Arg Ile
               155                 160                 165

ATG TCC AAG TCA GCT GCC TTA GAT TGT GCC CTA AAG GAC TAC GAT      540
Met Ser Lys Ser Ala Ala Leu Asp Cys Ala Leu Lys Asp Tyr Asp
               170                 175                 180

GTT CGG GTA AAC ACT GTT CAC CCT GGC TAC ATC AAG ACA CCA TTG      585
Val Arg Val Asn Thr Val His Pro Gly Tyr Ile Lys Thr Pro Leu
               185                 190                 195

GTT GAT GAC CTA CCA GGG GCC GAA GAA GCG ATG TCA CAA CGG ACC      630
Val Asp Asp Leu Pro Gly Ala Glu Glu Ala Met Ser Gln Arg Thr
               200                 205                 210

AAG ACG CCA ATG GGC CAT ATC GCT GAA CCT AAC GAT ATT GCC TAC      675
Lys Thr Pro Met Gly His Ile Ala Glu Pro Asn Asp Ile Ala Tyr
               215                 220                 225

ATC TGT GTT TAC TTG GCT TCT AAC GAA TCT AAA TTT GCA ACG GGT      720
Ile Cys Val Tyr Leu Ala Ser Asn Glu Ser Lys Phe Ala Thr Gly
               230                 235                 240

TCT GAA TTC GTA GTT GAC GGT GGC TAC ACT GCT CAA                  756
Ser Glu Phe Val Val Asp Gly Gly Tyr Thr Ala Gln
               245                 250

(2) INFORMATION FOR SEQ ID NO: 8:

(i) SEQUENCE CHARACTERISTICS:
        (A) LENGTH: 252 amino acids
        (B) TYPE: amino acid
        (D) TOPOLOGY: linear (ii) MOLECULE TYPE: protein (xi) SEQUENCE DESCRIPTION: SEQ ID NO: 8:

Met Ser Asn Arg Leu Asp Gly Lys Val Ala Ile Ile Thr Gly Gly
  1               5                  10                  15

Thr Leu Gly Ile Gly Leu Ala Ile Ala Thr Lys Phe Val Glu Glu
                 20                  25                  30

Gly Ala Lys Val Met Ile Thr Gly Arg His Ser Asp Val Gly Glu
                 35                  40                  45

Lys Ala Ala Lys Ser Val Gly Thr Pro Asp Gln Ile Gln Phe Phe
                 50                  55                  60

Gln His Asp Ser Ser Asp Glu Asp Gly Trp Thr Lys Leu Phe Asp
                 65                  70                  75

Ala Thr Glu Lys Ala Phe Gly Pro Val Ser Thr Leu Val Asn Asn
                 80                  85                  90
```

Ala Gly Ile Ala Val Asn Lys Ser Val Glu Glu Thr Thr Thr Ala
                 95                 100                105

Glu Trp Arg Lys Leu Leu Ala Val Asn Leu Asp Gly Val Phe Phe
            110                 115                120

Gly Thr Arg Leu Gly Ile Gln Arg Met Lys Asn Lys Gly Leu Gly
            125                 130                135

Ala Ser Ile Ile Asn Met Ser Ser Ile Glu Gly Phe Val Gly Asp
            140                 145                150

Pro Ser Leu Gly Ala Tyr Asn Ala Ser Lys Gly Ala Val Arg Ile
            155                 160                165

Met Ser Lys Ser Ala Ala Leu Asp Cys Ala Leu Lys Asp Tyr Asp
            170                 175                180

Val Arg Val Asn Thr Val His Pro Gly Tyr Ile Lys Thr Pro Leu
            185                 190                195

Val Asp Asp Leu Pro Gly Ala Glu Glu Ala Met Ser Gln Arg Thr
            200                 205                210

Lys Thr Pro Met Gly His Ile Ala Glu Pro Asn Asp Ile Ala Tyr
            215                 220                225

Ile Cys Val Tyr Leu Ala Ser Asn Glu Ser Lys Phe Ala Thr Gly
            230                 235                240

Ser Glu Phe Val Val Asp Gly Gly Tyr Thr Ala Gln
            245                 250

(2) INFORMATION FOR SEQ ID NO: 9:

(i) SEQUENCE CHARACTERISTICS:
        (A) LENGTH: 251 amino acids
        (B) TYPE: amino acid
        (D) TOPOLOGY: linear (ii) MOLECULE TYPE: peptide (xi) SEQUENCE DESCRIPTION: SEQ ID NO: 9:

Thr Asp Arg Leu Lys Gly Lys Val Ala Ile Val Thr Gly Gly Thr
 1               5                  10                 15

Leu Gly Ile Gly Leu Ala Ile Ala Asp Lys Phe Val Glu Glu Gly
            20                  25                 30

Ala Lys Val Val Ile Thr Gly Arg His Ala Asp Val Gly Glu Lys
            35                  40                 45

Xaa Xaa Xaa Xaa Xaa Xaa Xaa Xaa Xaa Xaa Xaa Xaa Xaa Xaa Xaa
            50                  55                 60

Xaa Xaa Xaa Xaa Xaa Xaa Xaa Xaa Xaa Xaa Xaa Leu Phe Asp Ala
            65                  70                 75

Thr Glu Glu Ala Phe Gly Pro Val Thr Thr Val Val Asn Asn Ala
            80                  85                 90

Gly Ile Ala Val Asn Lys Ser Val Glu Asp Thr Thr Thr Glu Glu
            95                 100                105

Trp Arg Lys Leu Leu Ser Val Asn Leu Asp Gly Val Phe Phe Gly
            110                115                120

Thr Arg Leu Gly Ile Gln Ala Met Lys Xaa Xaa Gly Leu Gly Ala
            125                130                135

Ser Ile Ile Asn Met Ser Ser Ile Glu Gly Phe Val Gly Asp Pro
            140                145                150

Thr Leu Gly Ala Tyr Asn Ala Ser Lys Gly Ala Val Arg Ile Met
            155                160                165

-continued

```
Ser Lys Ser Ala Ala Leu Asp Cys Ala Leu Lys Asp Tyr Asp Val
            170                 175                 180

Arg Val Asn Thr Val His Pro Gly Tyr Ile Lys Thr Pro Leu Val
            185                 190                 195

Asp Asp Leu Glu Gly Ala Glu Glu Met Met Ser Gln Arg Thr Lys
            200                 205                 210

Thr Pro Met Gly His Ile Gly Glu Pro Asn Asp Ile Ala Tyr Ile
            215                 220                 225

Cys Val Tyr Leu Ala Ser Asp Glu Thr Lys Phe Ala Thr Gly Ala
            230                 235                 240

Glu Phe Val Val Asp Gly Gly Tyr Thr Ala Gln
            245                 250
```